United States Patent [19]

Prasad et al.

[11] 3,966,917
[45] June 29, 1976

[54] PLATELET AGGREGATION INHIBITORS
[75] Inventors: Raj Nandan Prasad, Pierrefonds, Canada; Herman Hal Stein, Skokie, Ill.
[73] Assignee: Abbott Laboratories, North Chicago, Ill.
[22] Filed: June 26, 1975
[21] Appl. No.: 590,548

Related U.S. Application Data
[60] Continuation-in-part of Ser. No. 492,949, July 30, 1974, Pat. No. 3,914,414, which is a division of Ser. No. 370,084, June 14, 1973, Pat. No. 3,864,483, which is a division of Ser. No. 236,980, March 22, 1972, abandoned, which is a continuation-in-part of Ser. No. 125,893, March 18, 1971, abandoned.

[52] U.S. Cl. ............................ 424/180; 260/211.5 R
[51] Int. Cl.² ........................................ A61K 27/12
[58] Field of Search ............... 260/211.5 R; 424/180

[56] References Cited
UNITED STATES PATENTS
3,697,504  10/1972  Schmidt ................. 260/211.5 R
3,864,483   2/1975  Stein et al. ........................ 424/180

FOREIGN PATENTS OR APPLICATIONS
2,034,785  1/1972  Germany .................. 260/211.5 R

*Primary Examiner*—Johnnie R. Brown
*Attorney, Agent, or Firm*—Robert L. Niblack; Vincent A. Mallare

[57] ABSTRACT

Adenosine-5'-carboxamides which are effective as platelet aggregation inhibitors and represented by the formula

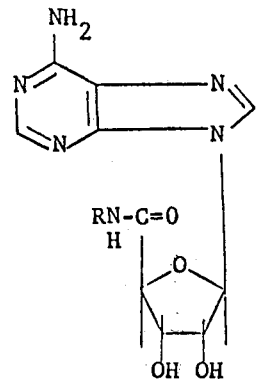

wherein R is hydrogen, loweralkyl, lowercycloalkyl, loweralkenyl, or lowerhydroxyalkyl.

7 Claims, No Drawings

PLATELET AGGREGATION INHIBITORS

CROSS-REFERENCE TO RELATED APPLICATION

This application is a continuation-in-part of copending application Ser. No. 492,949, filed July 30, 1974, now U.S. Pat. No. 3,914,414 which is a divisional of application, Ser. No. 370,084 filed June 14, 1973, now U.S. Pat. No. 3,864,483 issued Feb. 4, 1975, which is a division of application, Ser. No. 236,980 filed Mar. 22, 1972, now abandoned which is a continuation-in-part of a copending application, Ser. No. 125,893, filed Mar. 18, 1971, now abandoned.

DETAILED DESCRIPTION OF THE INVENTION

This invention relates to adenosine derivatives and more particularly to adenosine-6'-carboxamides as useful platelet aggregation inhibitors.

The compounds of this invention are represented by the formula

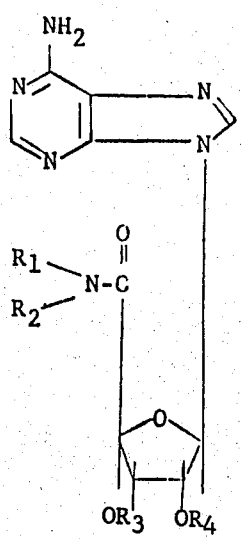

wherein $R_1$ and $R_2$ are each selected from the group consisting of hydrogen, loweralkyl, lowerhaloalkyl, lowerhydroxyalkyl, lowercycloalkyl, loweralkylcycloalkyl, loweralkenyl, lowerhaloalkenyl, lowerhydroxyalkenyl, loweralkynyl, lowerhaloalkynyl, benzylamino, phenyl, loweralkylphenyl, loweralkoxyloweralkyl, substituted phenyl or 2-methylfuran, or di($C_1-C_4$)alkylamino ($C_1-C_4$)alkyl, adamantyl; or $R_1$ and $R_2$ taken together form a 5 or 6 membered heterocyclic moiety; $R_3$ and $R_4$ are hydrogen or acyl, or taken together form an isopropylidene or a benzylidene group; or a pharmaceutically acceptable acid addition salt thereof. Compounds wherein $R_3$ and $R_4$ are hydrogen are useful in treating cardiovascular disorder and are particularly useful as anti-hypertensive and anti-anginal agents. A number of amides also exhibit anti-inflammatory activity.

The compounds of the present invention which are particularly useful as platelet aggregation inhibitors, include those represented by the formula

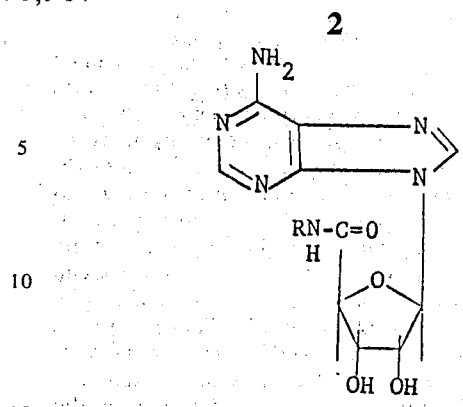

wherein R is H, $CH_3$, $CH_3CH_2$, $(CH_3)_2CH$,

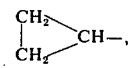

$CH_2=CHCH_2$, or $CH_3(CH_2)_2$.

Representative compounds of this invention include: adenosine-5'-carboxamide; adenosine-5'-(N-methyl)-carboxamide; adenosine-5'-(N-iso-propyl)carboxamide; adenosine-5'-(N-ethyl)-carboxamide; adenosine-5'-(N-n-propyl)carboxamide; adenosine-5'-(N-iso-butyl)carboxamide; adenosine-5'-(N-n-butyl)carboxamide; adenosine-5'-(N-n-pentyl)carboxamide; adenosine-5'-(N-iso-pentyl)carboxamide; adenosine-5'-(N,N-dimethyl)carboxamide; adenosine-5'-(N,N-diethyl)carboxamide; adenosine-5'-(N,N-diisopropyl)carboxamide; adenosine-5'-(N-methyl-N-ethyl)carboxamide; adenosine-5'-(N-cyclobutyl)-carboxamide; adenosine-5'-(N-cyclopropylmethyl)carboxamide; adenosine-5'-(N-propargyl)-caboxamide; adenosine-5'-(N-allyl)carboxamide; and adenosine-5'-(N-ethoxyethyl)carboxamide; adenosine-5'-(N,N-dicyclopropylmethyl)carboxamide; adenosine-5'-(N,N-dichloroethyl)carboxamide.

The compounds of this invention are useful as blood pressure lowering agents when administered to hypertensive patients in dosages of from 0.001–25 mg./kg. of body weight daily. The compounds are also useful in the management and treatment of angina pectoris when administered to patients suffering from or prone to such attacks in dosages of from 0.001–25 mg./kg. of body weight daily. In both instances, it is preferred to administer the compounds orally, however, the compounds may also be administered via intravenous administration. The compounds can be administered in single doses, however, it is preferred that they can be administered in divided doses, i.e., 3 – 4 times daily.

In addition to their cardiovascular activity, a number of amides exhibit anti-inflammatory activity at dosages of 0.04 to 100 mg./kg. of body weight, with a number of the compounds having an $ED_{25}$ in the paw edema test of under 1 mg./kg.

The compounds of this invention can be prepared by converting adenosine-5'-carboxylic acid (prepared from 2',3'-isopropylidene adenosine according to the method described by Harmon et al., Chem. Ind. 1969, 1141 to the corresponding acid chloride by reacting it with thinoyl chloride and then reacting the acid chloride with ammonia or an appropriately substituted alkylamine such as methylamine, dimethylamine and the like. It will be obvious to those skilled in the art that other well-known procedures can also be employed to prepare the compounds of this invention.

The 2′,3′-hydroxyl groups of the starting acid can be temporarily blocked by using the protective groups which are conventional in sugar chemistry. The protecting groups can be acyl groups, preferably acetyl or benxoyl groups, or ketals, such as the 2′,3′-isopropylidene or benzylidene, which can be converted back to the 2′,3′-dihydroxy compounds by methods well-known in the art, preferably after the conversion of the acid chloride to the amide. The 2′,3′-isopropylidene adenosine starting material is commercially available from Pfanstiehl Corporation, North Chicago, Illinois and the preparation thereof is well known. A number of the intermediates also exhibit cardiovascular activity.

The preferred synthetic route is represented by the following reaction scheme:

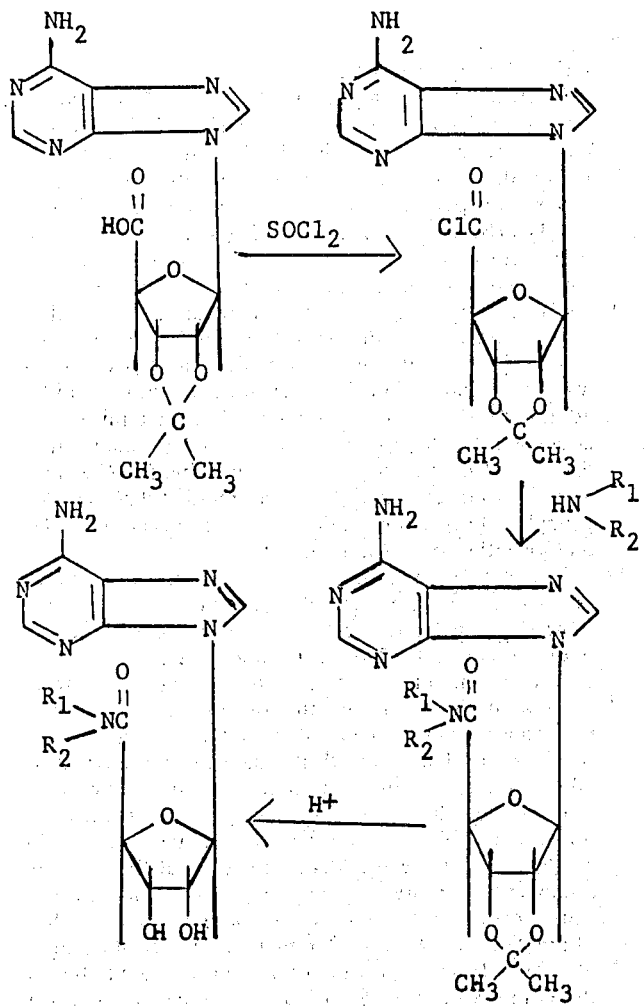

The following examples further illustrate the present invention:

EXAMPLE 1

2′,3′-Isopropylidene Adenosine-5′-Carboxylic Acid Chloride

2′,3′-Isopropylidene adenosine-5′-carboxylic acid (12.8 g.) [prepared according to the method of R. E. Harmon, et al., Chem. Inc. London, No. 33, 1141, (1969)] was added to an excess of thionyl chloride (70 ml.) at 0°C. The mixture was stirred for 1 hour at 0°C. and then the temperature was allowed to go up to room temperature for another hour. The clear solution was poured, in a thin stream, onto a large volume of well stirred dry ether. The yellow precipitate of 2′,3′-isopropylidene adenosine-5′-carboxylic acid chloride, m.p. 190°–195° dec. was filtered and washed with an excess of dry ether. This material was used directly for the preparation of the amides without any further purification.

EXAMPLE 2

Adenosine-5′-Carboxamide

A mixture of 6.8 g. of 2′,3′-isopropylidene adenosine-5′-carboxylic acid chloride and 50 ml. of liquid anhydrous ammonia was stirred for two (2) hours at -60° to 50°C. At the end of this time the ammonia was allowed to evaporate off at room temperature. The residue was triturated with cold aqueous sodium bicarbonate solution (1N). The resulting insoluble solid was filtered, washed with cold water and recrystallized from ethanol to yield 3.5 g. (55%) of crude 2′,3′-isopropylidene adenosine-5′-carboxamide, m.p. 220°–222°. The amide was then mixed with 100 ml. of 1 N hydrochloric acid and maintained at a temperature of between 60°–70° for 45 minutes. The acidic solution was then cooled, neutralized with sodium bicarbonate and the mixture evaporated to dryness under reduced pressure. The residue was recrystallized three times from absolute ethanol to yield one gram of pure adenosine-5'-carboxamide, m.p. 245°–247°; $[\alpha]_D^{27°}$ −29°±0.9° (c, 1.08 in 1N HCl). Elemental analysis and nuclear magnetic resonance data confirmed the identity of the compound.

EXAMPLE 3

Adenosine-5'-(N-methyl)Carboxamide

2',3'-Isopropylidene adenosine-5'-[N-methylcarboxamide] (m.p. 264°–265°) was prepared according to the method of Example 2 from 2',3'-isopropylidene adenosine-5'-carboxylic acid chloride and an excess of dry liquid methylamine at −20° to −10°C. The 2',3'-isopropylidene group was cleaved by the use of 1N HCl at 60° for 45 minutes to give adenosine-5'-(N-methyl)carboxamide in 44% yield; m.p. 240°–241°; $[\alpha]_D^{27°}$ −23° ± 0.6° (c, 3.2 in 1N HCl). Elemental analysis and nuclear magnetic resonance data confirmed the identity of the compound.

EXAMPLE 4

Adenosine-5'-(N,N-dimethyl)Carboxamide 13.5 g. of 2',3'-isopropylidene adenosine-5'-carboxylic acid chloride was stirred with excess dry dimethylamine at −10°to 0°C. The clear solution was allowed to warm to room temperature. In about 3 hours the unreacted dimethylamine had evaporated off. The residue was washed with ether and dissolved in the minimum amount of cold aqueous NaHCO$_3$ solution (1). The basic aqueous solution so obtained was extracted five times with 50 ml. of chloroform. The chloroform extract was dried and evaporated under reduced pressure to give an amorphous solid. This solid was dissolved in dilute acetic acid, filtered (to remove a small amount of insoluble material) and the filtrate was extracted four times with 50 ml. of chloroform. The chloroform extract was dried and evaporated to dryness under reduced pressure to yield 6.0 g. (43%) of 2',3'-isopropylidene adenosine-5'-(N,N-dimethyl)carboxamide. The crude amide (m.p. 106°–110°) was dissolved in 100 ml. of 1N HCL and kept at 60°–70° for 45 minutes. The solution was then cooled, basified with NaHCO$_3$ and evaporated to dryness under reduced pressure.

The residue, upon recrystallization three times from absolute ethanol, gave 3.0 g. (23%) of adenosine-5'-(N,N-dimethyl)carboxamide as a monohydrate; m.p. 190°–191°; $[\alpha]_D^{27°}$ −17° ± 0.3° (c, 3 in 1N HCl). Elemental analysis and nuclear magnetic resonance data confirmed the identity of the compound.

EXAMPLE 5

Adenosine-5'-[(N-ethyl)-Carboxamide]

Freshly prepared 2',3'-isopropylidene adenosine-5'-carboxylic acid chloride (prepared from 6.4 g. of 2',3'-isopropylidene-5'-carboxylic acid) was stirred with excess of dry liquid ethyl amine at −50° to −35°. The clear redorange solution was allowed to warm up to room temperature and kept at this temperature for 15 hours. At the end of this period the excess of ethyl amine had evaporated off. The residue was triturated with cold aqueous NaHCO$_3$ solution. The white precipitate was filtered off and washed with a small amount of cold water to yield 3.1 g. (44.5%) of crude 2',3'-isopropylidene-5'-[(N-ethyl)-carboxamide] m.p. 225°–227°. R$_f$ 0.72 (silica gel) system: n.BuOH:H$_2$O: NH$_4$OH (86:14:5). The above amide was mixed with 80 ml. of 1 N HCL and kept at 65° for 45 minutes. The acidic solution was then cooled and basified with NaHCO$_3$. The mixture was then evaporated to dryness under reduced pressure, and the residue recrystallized twice from absolute ethanol and finally from water. The white crystalline product was dried in vacuo for 2 days over P$_2$O$_5$ at 70°–78° to give 0.9 g. (32 %) of adenosine-5'-[(N-ethyl)carboxamide] which melted slowly at 136°–172° and solidified again at 148°–150° and finally melted at 246°–247° (sharp). $[\alpha]_D^{26°}$ −163 (c, 0.92 in 1 N HCl); R$_f$ 0.51 (silica gel). System: n-BuOH: H$_2$O:NH$_4$OH (86:14:05); NMR (deuterated DMSO) peaks (in ppm) at 5.6 (2'-OH, 3'-OH), 7.4 (6C-NH$_2$); 8.8 (CONH); 3.2 (CH$_2$CH$_3$). Elemental analysis and NMR data confirmed the identity of the compound.

The following compounds are prepared according to the method of Example 4, substituting the appropriate amine for diethylamine except that Examples 29 and 31 were made as follows:

EXAMPLE 29

2',3'-Diacetyl Adenosine-(5'-N-Cyclopropyl)Carboxamide

A solution of adenosine-(5'-N-cyclopropyl)carboxamide (3.0 g.) in pyridine (40 ml.) was cooled, diluted with acetic anhydride (15 ml.) and stirred at 37°–40° for two hours. At the end of this period, absolute ethanol was added to the reaction mixture and the mixture was evaporated under reduced pressure. The residue was diluted with absolute ethanol and the solution was evaporated again. This process was repeated a few times until an amorphous residue was obtained. The residue was triturated a few times with ether, filtered, dissolved in dry methanol and refluxed overnight. The methanolic solution was evaporated to dryness and the residue (2.8 g.) taken up in chloroform and applied on a 100 ml. silica gel column. The product was eluted with ethyl acetate and the fractions 9 to 14 (R$_f$ 0.62; n-butanol/H$_2$O) were pooled together (1.4 g.; m.p. 99°–105°).

Anal. Calcd. for C$_{17}$H$_{20}$N$_6$O$_6$:
Requires: C, 50.49; H, 4.99.
Found: C, 50,38; H, 5.16.

IR spectra of the compound showed the ester and amide peaks. NMR spectra confirmed the structure.

EXAMPLE 31

2',3'-Diacetyl Adenosine-(5'-N-Ethyl) Carboxamide

A mixture of adenosine-5'-(N-ethyl) carboxamide (2.0 g,; 0.0065 mole) and acetic anhydride (15 ml) in pyridine (25 ml.) was kept at 40°C for two hours. The mixture was diluted with absolute ethanol and the solution was evaporated under reduced pressure. This process was repeated twice. The residual oil solidified on trituration with ether. The solid was dissolved in methanol, stirred with Rexyn 203 (OH form) for five minutes under UV light, filtered through celite and the solvent was removed under reduced pressure. Ether was added to the residue and the product was filtered (1.4 g.; m.p. 96°–102°).

Anal. Calcd. for $C_{16}H_{20}N_6O_6$:
Requires: C, 48.98; H, 5.14; O, 24.47.
Found: C, 47.96; H, 5.19; O, 24.58, IR spectra showed the presence of ester and amide groups. NMR spectrum was consistent with the structure of the compound.

| Example | $R_1$ | $R_2$ | Mp°C. | Recrystn Solvent | $[\alpha]_D^{26°}$ Rotation | C/1NHCl | $R_f^b$ |
|---|---|---|---|---|---|---|---|
| 6 | —$C_2H_5$ | H | 246–247 | $H_2O$ | −16.3±0.54° | 0.92 | 0.51 |
| 7 | —$C_2H_4$—O—$C_2H_5$ | H | 107–110 | EtOH | −7.4±0.9° | 0.54 | 0.44 |
| 8 | —CH(CH$_3$)$_2$ | H | 137–141 | EtOH | −9±2.2° | 0.223 | 0.53 |
| 9 | —$(CH_2)_5CH_3$ | H | 104–106 | DMF | −8.9±1.5° | 0.334 | 0.56 |
| 10 | —$CH_2$—CH=$CH_2$ | H | 223–224 | EtOH | −13.5±1.4° | 0.369 | 0.50 |
| 11 | —$CH_2$—C≡CH | H | 135–137 | EtOH | −27.5±0.5° | 0.44 | 0.44 |
| 12 | cyclopropyl | H | 249–250 | EtOH | −6.8±0.8° | 0.584 | 0.47 |
| 13 | —$CH_2$—phenyl | H | 130–133 | $H_2O$ | −6.3±1.5° | 0.315 | 0.55 |
| 14 | —$(CH_2)_3CH_3$ | H | 125 | MeOH-Acetone | | | |
| 15 | —$(CH_2)_2CH_3$ | H | 220–222 | MeOH-Acetone-Ether | | | |
| 16 | —CH(CH$_2$CH$_3$)$_2$ | H | a | MeOH-EtOEt | −1.6±0.8° | 0.63 | |
| 17 | —$CH_2COOC_2H_5$ | H | 165–170 | Acetone-Ether | −3.7±0.23° | 2.16 | | a no sharp melting point
bTLC was done on Eastman 6060 Silica Gel Chromagram Sheet with Fluorescent indicator. Solvent System used was: n-BuOH:NH$_4$OH:H$_2$O=86:5:14

| Example Contd. | Empirical Formula | ANALYSES Calculated | | | | Found | | | |
|---|---|---|---|---|---|---|---|---|---|
| | | C | H | N | O | C | H | N | O |
| 6 | $C_{12}H_{16}N_6O_4 \cdot 1/2H_2O$ | 45.42 | 5.40 | 26.48 | 22.68 | 45.76 | 5.87 | 25.51 | 22.48 |
| 7 | $C_{14}H_{20}N_6O_5$ | 47.73 | 5.72 | 23.85 | 22.70 | 47.49 | 5.85 | 24.05 | 23.01 |
| 8 | $C_{13}H_{18}N_6O_4$ | 48.49 | 5.62 | 26.05 | 19.83 | 48.28 | 5.78 | 26.25 | 20.21 |
| 9 | $C_{16}H_{24}N_6O_4 \cdot 1/2H_2O$ | 51.47 | 6.75 | 22.51 | 19.28 | 51.52 | 6.69 | 22.41 | 19.13 |
| 10 | $C_{13}H_{16}N_6O_4 \cdot H_2O$ | 46.20 | 5.36 | 24.82 | 23.62 | 46.28 | 5.58 | 24.90 | 24.00 |
| 11 | $C_{13}H_{14}N_6O_4$ | 49.10 | 4.43 | 26.38 | 20.09 | 49.15 | 4.60 | 26.59 | 20.48 |
| 12 | $C_{13}H_{16}N_6O_4$ | 48.79 | 5.83 | 26.22 | 19.96 | 48.98 | 5.52 | 25.81 | 19.41 |
| 13 | $C_{12}H_{18}N_6O_4$ | 55.13 | 4.90 | 22.69 | 17.28 | 54.83 | 5.00 | 22.91 | 17.71 |
| 14 | $C_{14}H_{20}N_6O_4$ | 49.98 | 5.99 | 24.98 | 19.02 | 50.12 | 6.06 | 25.14 | 19.35 |
| 15 | $C_{13}H_{18}N_6O_4 \cdot CH_3OH$ | 47.44 | 6.25 | 23.71 | 22.57 | 47.00 | 5.80 | 24.86 | 22.69 |
| 16 | $C_{15}H_{22}N_6O_4$ | 51.41 | 6.33 | 23.98 | 18.26 | 50.39 | 6.36 | 23.55 | 17.36 |
| 17 | $C_{15}H_{20}N_6O_4$ | 51.71 | 5.78 | 24.12 | 18.37 | 51.51 | 6.06 | 24.17 | 18.75 |

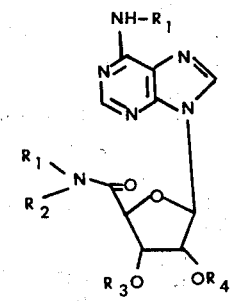

| Example | $R_1$ | $R_2$ | $R_3$ | $R_4$ | MP°C | $[\alpha]_D^{26°}$ Rotation | c | Solvent |
|---|---|---|---|---|---|---|---|---|
| 18 | H | 2,6-dimethylphenyl | | H | H | 203 | +14.8°±2° | 1.7 | 1N.HCl |

-continued

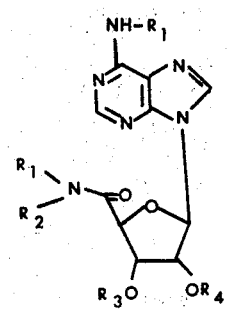

| Example | R₁ | R₂ | R₃ | R₄ | MP°C | Rotation | $[\alpha]_D^{26°}$ c | Solvent |
|---|---|---|---|---|---|---|---|---|
| 19 | H | (tolyl) | H | H | 175–79 | −3.3°±1° | 1.5 | CH₃COOH |
| 20 | H | ⌬-CH₂NH- | H | H | 245–47 | −18°±2° | 0.223 | 1N.HCl |
| 21 | H | HOCH₂CH₂— | H | H | 196–98 | −28.8°±1° | 1.6 | 1N.HCl |
| 22 | H | ⌬-OCH₂CH₂— | H | H | 125–29 | +50°±3° | 0.74 | 1N.HCl |
| 23 | H | (C₂H₅)₂NCH₂CH₂— | H | H | 194–79 | −20°±2° | 0.97 | EtOH |
| 24 | CH₂=CH—CH₂ | CH₂=CH—CH₂— | H | H | 224–27 | −50°±3° | 0.8 | 1N.HCl |
| 25 | H | (CH₃)₂NCH₂CH₂— | H | H | 165–67 | −44°±2° | 0.8 | H₂O |
| 26 | H | CH₂=C(CH₃)—CH₂— | H | H | 198–200 | −10°±1° | 1.0 | 1N.HCl |
| 27 | H | CH₃—CH(OH)—CH₂— | H | H | 188 dec | −42°±2° | 0.6 | H₂O |
| 28 | H | (2,5-diOCH₃-C₆H₃)-CH₂CH₂- | | | 104–106 | −40°±3° | 1.2 | H₂O |
| 29 | H | cyclopropyl | CH₃C(O)— | CH₃C(O)— | 78–87 | −17.3°±2° | 0.58 | EtOH |
| 30 | H | cyclopropyl-CH₂- | H | H | 216–18 | −17.7°±2° | 0.56 | 1N.HCl |
| 31 | H | CH₃CH₂— | CH₃C(O)— | CH₃C(O)— | 96–102 | −19°±2° | 1.8 | H₂O |
| 32 | H | CH₂=CH—CH₂— | isopropylidene | | 214–16 | −3.6°±0.8° | 1.4 | 1N.HCl |
| 33 | H | CH₃CH₂— | isopropylidene | | 225–29 | −22°±2° | 0.89 | 1N.HCl |
| 34 | H | cyclopropyl | isopropylidene | | 185–87 | −5°±1° | 1.0 | EtOH |

| Examples Contd. | R_f(1) | Empirical Formulae and Microanalysis |
|---|---|---|
| 18 | 0.62 | $C_{18}H_{20}N_6O_4 \cdot 3H_2O$<br>Calcd. C, 49.31; H, 5.97; N, 19.17; O, —<br>Found. C, 49.73; H, 4.29; N, 19.45; O, — |
| 19 | 0.61 | $C_{20}H_{27}N_6O_4$<br>Calcd. C, 57.82; H, 6.55; N, 20.23; O, 15.40 |

| Examples Contd. | $R_f(1)$ | Empirical Formulae and Microanalysis |
|---|---|---|
| | | Found. C, 57.51; H, 6.42; N, 20.01; O, 15.80 |
| 20 | 0.57 | $C_{17}H_{19}N_7O_4 \cdot H_2O$ |
| | | Calcd. C, 50.62; H, 5.24; N, 24.30; O, 19.82 |
| | | Found. C, 50.96; H, 4.56; N, 23.41; O, 19.19 |
| 21 | 0.32 | $C_{12}H_{16}N_6O_5$ |
| | | Calcd. C, 44.44; H, 4.97; N, 25.91; O, 24.67 |
| | | Found. C, 44.64; H, 5.14; N, 25.55; O, 24.70 |
| 22 | 0.62 | $C_{18}H_{20}N_6O_5 \cdot 1/2H_2O$ |
| | | Calcd. C, 52.81; H, 5.17; N, 20.53; O, 21.49 |
| | | Found. C, 52.21; H, 4.90; N, 20.38; O, 20.72 |
| 23 | — | $C_{16}H_{25}N_7O_4$ |
| | | Calcd. C, 50.65; H, 6.64; N, 25.84; O, — |
| | | Found. C, 50.97; H, 6.81; N, 25.93; O, — |
| 24 | 0.62 | $C_{16}H_{20}N_6O_4$ |
| | | Calcd. C, 53.33; H, 5.59; N, 23.32; O, — |
| | | Found. C, 53.25; H, 5.77; N, 27.18; O, — |
| 25 | — | $C_{14}H_{21}N_7O_4$ |
| | | Calcd. C, 47.86; H, 6.02; N, 27.90; O, — |
| | | Found. C, 47.68; H, 6.01; N, 27.91; O, — |
| 26 | 0.59 | $C_{14}H_{18}N_6O_4$ |
| | | Calcd. C, 50.30; H, 5.39; N, 25.15; O, 19.16 |
| | | Found. C, 50.50; H, 5.62; N, 24.97; O, 19.46 |
| 27 | 0.43 | $C_{13}H_{18}N_6O_5(2)$ |
| 28 | 0.35 | $C_{20}H_{24}N_6O_6(2)$ |
| 29 | 0.51 | $C_{17}H_{20}N_6O_6$ |
| | | Calcd. C, 50.49; H, 4.99; N, —; O, — |
| | | Found. C, 50.38; H, 5.16; N, —; O, — |
| 30 | — | $C_{14}H_{18}N_6O_4 \cdot EtOH$ |
| | | Calcd. C, 50.52; H, 6.36; N, 22.09; O, 21.03 |
| | | Found. C, 49.80; H, 6.32; N, 23.18; O, 21.03 |
| 31 | — | $C_{16}H_{20}N_6O_6$ |
| | | Calcd. C, 48.98; H, 5.14; N, —; O, 24.47 |
| | | Found. C, 47.96; H, 5.19; N, —; O, 24.58 |
| 32 | — | $C_{16}H_{20}N_6O_4$ |
| | | Calcd. C, 53.33; H, 5.59; N, 23.32; O, — |
| | | Found. C, 53.53; H, 5.68; N, 23.39; O, — |
| 33 | 0.66 (3) | $C_{15}H_{20}N_6O_4$ |
| | | Calcd. C, 51.72; H, 5.79; N, 24.12; O, — |
| | | Found. C, 51.74; H, 5.82; N, 24.47; O, — |
| 34 | — | $C_{16}H_{20}N_6O_4$ |
| | | Calcd. C, 53.33; H, 5.59; N, 23.32; O, — |
| | | Found. C, 53.39; H, 5.48; N, 23.43; O, — |

1. $R_f$ values are obtained from the TLC. Unless otherwise specified, solvent system used was: nBuOH:NH₄OH: H₂O: 86:5:14. All compounds had a single spot in the TLC.
2. The total of the percentage composition of all the elements (C, H, N & O) determined by the analyst was only 95% or less. The compounds had a single spot in the TLC. Their structures were followed by the infrared spectra and confirmed by the NMR.
3. Solvent system: n-Butanol saturated with water.

While all of the compounds of this invention exhibit cardiovascular activity, only certain of the compounds exhibit anti-inflammatory activity. The following table summarizes the anti-inflammatory activity in anti-inflammatory rat paw edema assay:

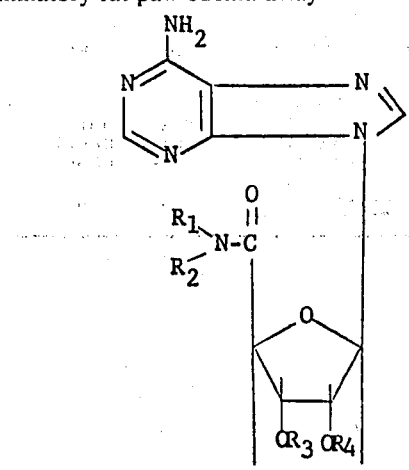

| $R_1$ | $R_3$ | $R_4$ | $ED_{25}$(mg./kg.) |
|---|---|---|---|
| $-C_2H_5$ | H | H | 0.137 |
| $-CH_2-CH=CH_2$ | H | H | 50 |
| ◁ | H | H | 1.28 |
| $-CH_2-C=CH_2$ $\quad CH_3$ | H | H | 55 |
| $-CH_2\overset{OH}{C}H-CH_3$ | H | H | 75 |
| ◁ | acetyl | acetyl | 1.3 |

$R_2$ is H in each of the above compounds.

As in the compounds which exhibit an antiinflammatory activity, there are certain compounds of the present invention which inhibit platelet aggregation in a patient having symptoms of a thrombosis. The following table summarizes the inhibition of platelet aggregation of certain compounds of this invention.

The results are of in vitro administration of molar concentrations (M × 10⁶) of the compounds:

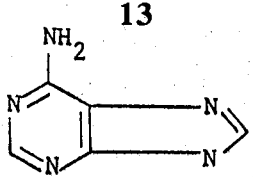

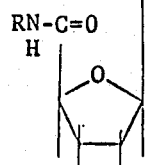

| Compound | R | Concentration M × 10⁶ | Percent (%) Inhibition |
|---|---|---|---|
| A | H | 4.8 | 24 |
| B | $CH_3$ | 4.8 | 60 |
| C | $CH_3CH_2$ | 0.95 | 34 |
|   |   | 4.8 | 74 |
| D | $(CH_3)_2CH$ | 4.8 | 36 |
| E | 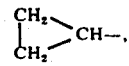 | 0.95 | 45 |
|   |   | 4.8 | 79 |
| F | $CH_2=CHCH_2$ | 4.8 | 46 |
| G | $CH_3(CH_2)_2$ | 4.8 | 34 |
| Control - Adenosine |   | 0.95 | 6 |
|   |   | 4.8 | 31 |

The compounds of this invention can be formulated into various pharmaceutically acceptable dosage forms such as tablets, capsules, pills and the like for immediate or sustained releases by combining the active compound with suitable pharmaceutically acceptable carriers or diluents according to methods well-known in the art. Such dosage forms may automatically include excipients, binders, fillers, flavoring and sweetening agents and other therapeutically inert ingredients necessary in the formation of the desired preparation.

Preparations for parenteral administration include sterile, aqueous or non-aqueous solutions, suspensions or emulsions which are well-known in the art.

We claim:

1. A method of inhibiting platelet aggregation in a patient having symptoms of a thrombosis, comprising administering to said patient a therapeutic amount of a compound of the formula:

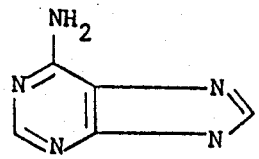

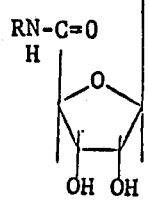

wherein R is H, $CH_3$, $CH_3CH_2$, $(CH_3)_2CH$,

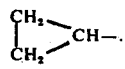

$CH_2=CHCH_2$, or $CH_3(CH_2)_2$.

2. The method of claim 1 wherein R is methyl.
3. The method of claim 1 wherein R is $CH_3CH_2$.
4. The method of claim 1 wherein R is $(CH_3)_2CH$.
5. The method of claim 1 wherein R is

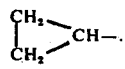

6. The method of claim 1 wherein R is $CH_2=CHCH_2$.
7. The method of claim 1 wherein R is $CH_3(CH_2)_2$.

* * * * *